United States Patent [19]

Gubelmann

[11] Patent Number: 4,950,809

[45] Date of Patent: Aug. 21, 1990

[54] PROCESS FOR PREPARING HYDROXYLATED AROMATIC DERIVATIVES BY THE BAEYER-VILLIGER REACTION

[75] Inventor: Michel Gubelmann, Lyon, France

[73] Assignee: Rhone-Poulenc Chimie, Courbevoie, France

[21] Appl. No.: 281,408

[22] Filed: Dec. 8, 1988

[30] Foreign Application Priority Data

Dec. 11, 1987 [FR] France ................... 87 17323

[51] Int. Cl.$^5$ ............................................ C07C 37/60
[52] U.S. Cl. .................................. 568/741; 568/771; 568/803
[58] Field of Search .................. 568/771, 803, 741

[56] References Cited

U.S. PATENT DOCUMENTS 3,278,562 10/1966 Thigpen et al. .............. 568/771
3,927,122 12/1975 Bourdin et al. .............. 568/803
3,927,123 12/1975 Bourdin et al. .............. 568/803

FOREIGN PATENT DOCUMENTS 178929 4/1986 European Pat. Off. .

OTHER PUBLICATIONS

W. von F. Doering and L. Speers, J. Am. Chemical Soc'y, vol. 72, (1959), pp. 5515–5518.

*Primary Examiner*—Werren B. Lone
*Attorney, Agent, or Firm*—Finnegan, Henderson, Farabow, Garrett and Dunner

[57] ABSTRACT

A process for preparing a hydroxylated aromatic compound by the Baeyer-Villiger reaction. In a first stage, a solution of peracetic acid is formed. In a second stage, an aryl ketone and/or an aromatic aldehyde is contacted with the above solution for a time sufficient to obtain the hydroxylated aromatic compound. The hydroxylated compound obtained can be used in the pharmaceutical, plant-protection or polymer chemical industries.

19 Claims, No Drawings

PROCESS FOR PREPARING HYDROXYLATED AROMATIC DERIVATIVES BY THE BAEYER-VILLIGER REACTION

The present invention relates to a process for preparing hydroxylated aromatic compounds It relates more particularly to a process for preparing a hydroxylated aromatic compound from aromatic ketones or aromatic aldehydes by the Baeyer-Villiger reaction.

It has been known for a very long time, as described, for example, by W. von E. Doering and Louise Speers (J. Am. Chemical Soc'y 72, (1950), pp. 5515–5518), to prepare phenols from aromatic ketones by the Baeyer-Villiger technique using peracetic acid as the peracid, the reaction being catalyzed by the addition of sulfuric acid.

Many publications since the beginning of the century have described the Baeyer-Villiger reaction on various ketones such as acetophenones and cyclic ketones, under varied conditions including employing acid catalysts, such as sulfuric or phosphoric acid, and with regard to the absence of water and of hydrogen peroxide in the peracetic solution.

The European Patent Application published under No. EP 178,929 states that hydroquinone or its derivatives can be prepared from para-hydroxy-acetophenone by the Baeyer-Villiger reaction using peracetic acid as the oxidizing agent in the presence of sulfuric acid in an amount less than 0.1% by weight relative to the peracetic acid employed. The peracetic acid solution is preferably added to the ketone (description page 4 last line and page 9 line 29, and all the examples). The reaction temperature is between 20 and 150° in the description, but in all the examples it is 60° C. or 80° C.

The reaction conditions, that is to say the introduction of pure and distilled peracetic acid into the solution containing the ketone reagent, as well as the necessary purification of the peracetic acid by distillation, have always caused the industry to refrain from employing this technique. The safety standards demanded by the distillation of explosive reagents such as peracids have led us to discard the method described in that patent application.

Furthermore, above 80° C., the detonability of peracetic acid becomes still worse.

It is also known to purify peracids as described in French Patent No. 2,359,132, by a sequence of countercurrent extractions, first with benzene and then with water, followed thereafter by the addition of a stabilizer. The peracid solution obtained contains, at the end of the extraction, a significant amount of water and of hydrogen peroxide. The process is unusable compared to the preferred embodiment of the present invention, since the purity of the peracid is not sufficient and the process is much too complicated. At the end of the reaction, hydrogen peroxide and water remain in the percarboxylic acid solution.

As a result, the industry has for a long time been seeking a method which would enable, on the one hand, the Baeyer-Villiger reaction to be used without distilling the peracetic acid and without using a liquid/liquid extraction technique, and, on the other hand, would make it possible to work at a temperature below 80° C.

The aforementioned patent application, that is to say the European Application published under number EP 178,929, gives examples only of the preparation of hydroquinones and derivatives thereof, as well as intermediates for making hydroquinones. The industry has for a long time been attempting to prepare, by the Baeyer-Villiger technique, phenol derivatives that are more difficult to prepare, namely para-halophenols and especially para-fluorophenol, which have never been prepared by this technique.

The present invention relates to a process for preparing a hydroxylated aromatic compound by the Baeyer-Villiger reaction, wherein in a first stage, a solution of peracetic acid is prepared by adding acetic anhydride to a solution of hydrogen peroxide in the presence of a strong acid catalyst, and in a second stage, an aryl ketone and/or an aromatic aldehyde is/are contacted with the above solution and the medium is maintained at a temperature below or equal to 40° C. for a time sufficient to obtain the hydroxylated aromatic compound. In other words, either at least one aryl ketone or at least one aromatic aldehyde alone may be added or a mixture of at least one aryl ketone and at least one aromatic aldehyde may be added.

Preferably, the first reaction stage also includes an aliphatic solvent having 1 to 6 carbon atoms and at least one halogen substituent.

The strong acid catalyst can be inorganic or organic. It may take a homogeneous or heterogeneous form. Exemplary strong acids include sulfuric acid, methanesulfonic and trifluoromethanesulfonic acids, trifluoroacetic acid, phosphoric acid and cationic resins of the Amberlyst ® and Nafion ® type, which are more fully described below.

Preferably, the amount of acid catalyst used in the first stage of the reaction ranges from about 0.5 to 5% by weight of the total weight of the reaction mixture of the first stage.

The Baeyer-Villiger reaction has been represented schematically according to the following reaction equations:

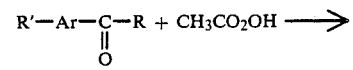

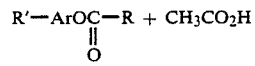

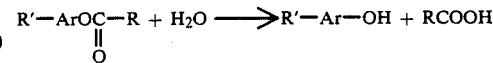

According to European published patent application 178,929, referred to above, the preparation of peracetic acid, pure, anhydrous and free from hydrogen peroxide, from commercial peracetic acid containing 40% by weight of peracetic acid, 13% of water, approximately 5% of hydrogen peroxide and 1% of sulfuric acid, is carried out by distillation at 40° C., under reduced pressure to avoid the risk of explosion as far as possible.

According to French Patent No. 2,359,132, the preparation of the pure peracids is carried out by countercurrent extraction of the commercial peracid with benzene.

These techniques always present risks. Thus, the present invention has enabled these dangers to be avoided by preparing the peracetic acid directly in the reaction chamber.

According to a preferred embodiment of the present invention, the inorganic or organic strong acid catalyst is introduced into the reactor in an aliphatic solvent having 1 to 6 carbon atoms and at least one halogen substituent. It is most preferable to use chlorinated aliphatic solvents having 1 to 2 carbon atoms, particularly dichloroethane.

Hydrogen peroxide is then added, followed by acetic anhydride. It is highly preferred that the addition be carried out in such a way that the total amount of acetic anhydride is in excess relative to the hydrogen peroxide so as not to allow either water or hydrogen peroxide to remain in the final solution. Preferably, solutions of peracetic acid in the aliphatic solvent not exceeding 35% by weight, more preferably from 15 to 25% by weight, and most preferably solutions containing 20% by weight, peracetic acid are thereby prepared.

The aryl ketone and/or aromatic aldehyde is/are added to this solution without any additional treatment.

The aryl ketone or aromatic aldehyde used preferably corresponds to the formula (I)

$(R')_n\text{-Ar-CO-R}$     (I)

in which:

Ar is a mono- or polycyclic, homo- or heterocyclic aromatic radical,

R' is a unit selected from alkyl radicals containing from 1 to 4 carbon atoms, alkoxy radicals containing from 1 to 4 carbon atoms and hydroxy, halo, acyloxy

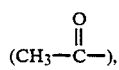
$(CH_3-\overset{\overset{O}{\|}}{C}-)$, alkoxycarbonyl, perhaloalkyl, perhaloalkoxy, nitro, phenyl and phenoxy radicals, wherein the phenyl and phenoxy radicals are unsubstituted or substituted with a substituent selected from hydroxyl, formyl

$(HC-)$, acyloxy and halo n is an integer equal to 0, 1 or 2, and

R is hydrogen, an alkyl group containing 1 to 4 carbon atoms or a phenyl group.

It is preferable to use aryl ketones or aromatic aldehydes in which Ar denotes a benzene radical, R denotes hydrogen or a methyl group and R' denotes fluorine.

Among compounds of formula (I), there may be mentioned, in particular:

compounds in which R = H
  benzaldehyde,
  ortho, meta and para-methylbenzaldehydes (tolualdehydes),
  ortho-, meta- and para-fluorobenzaldehydes,
  ortho-, meta- and para-chlorobenzaldehydes,
  ortho-, meta- and para-nitrobenzaldehydes,
  ortho-, meta- and para-trifluoromethylbenzaldehydes,
  ortho-, meta- and para-phenylbenzaldehydes,
  ortho-, meta- and para-(4-hydroxyphenyl)benzaldehydes,
  4,4'-biphenyldicarbaldehyde,
  4-acetyl-4'-biphenylcarbaldehyde,
  ortho-, meta- and para-hydroxybenzaldehydes,
  ortho-, meta- and para-methoxybenzaldehydes,
  ortho-, meta- and para-acetoxybenzaldehydes,
  ortho-, meta- and paraphenoxybenzaldehydes,
  ortho-, meta- and para-(4-hydroxyphenoxy)benzaldehydes,
  4,4'-diformyl-ortho-, -meta-, and -paradiphenyl ethers,
  4-acetyl-4'-formyldiphenyl ether,
  2-naphthaldehyde,
  4-methoxy-3-methylbenzaldehyde,
  4-methoxy-2-methylbenzaldehyde,
  methyl 6-formyl-3-indolecarboxylate,
  methyl 5-formyl-3-indolecarboxylate, compounds in which R = CH₃
  acetophenone,
  ortho-, meta- and para-methylacetophenones,
  ortho-, meta- and para-fluoroacetophenones,
  ortho-, meta- and para-chloroacetophenones,
  ortho-, meta- and para-nitroacetophenones,
  ortho-, meta- and para-trifluoromethylacetophenones,
  ortho-, meta- and para-phenylacetophenones,
  ortho0, meta- and para-(4-hydroxyphenyl)acetophenones,
  4-acetyl-4'-biphenylcarbaldehyde,
  4,4'-diacetylbiphenyl,
  ortho-, meta- and para-hydroxyacetophenones,
  ortho-, meta- and para-methoxyacetophenones,
  ortho-, meta- and para-acetoxyacetophenones,
  ortho-, meta- and para-phenoxyacetophenones,
  ortho-, meta- and para-(4-hydroxyphenoxy)acetophenones,
  4-acetyl-4'-formyldiphenyl ether,
  4,4'-diacetyldiphenyl ether,
  2-acetylnaphthalene,
  4-methoxy-3-methylacetophenone,
  4-methoxy-2-methylacetophenone,
  methyl 6-acetyl-3-indolecarboxylate,
  methyl 5-acetyl-3-indolecarboxylate, compounds in which R denotes a phenyl group
  ortho-, meta- and para-methylbenzophenones,
  ortho-, meta- and para-fluorobenzophenones,
  ortho-, meta- and para-chlorobenzophenones,
  ortho-, meta- and para-nitrobenzophenones,
  ortho-, meta- and para-trifluoromethylbenzophenones,
  ortho-, meta- and para-phenylbenzophenones,
  ortho-, meta- and para-(4-hydroxyphenyl)benzophenones,
  4-benzoyl-4'-biphenylcarbaldehyde,
  4-acetyl-4'-benzoylbiphenyl,
  ortho-, meta- and para-hydroxybenzophenones,
  ortho-, meta- and para-methoxybenzophenones,
  ortho-, meta- and para-acetoxybenzophenones,
  ortho-, meta- and para-phenoxybenzophenones,
  ortho-, meta- and para-(4-hydroxyphenoxy)benzophenones,
  4-benzoyl-4'-formyldiphenyl ether,
  2-benzoylnaphthalene,
  4-methoxy-3-methylbenzophenone,
  4-methoxy-2-methylbenzophenone,
  methyl 6-benzoyl-3-indolecarboxylate,
  methyl 5-benzoyl-3-indolecarboxylate.

For a better implementation of the invention, it is preferable to add the aryl ketone and/or aromatic aldehyde in an amount such that the ratio of the number of moles of peracetic acid per ketone or aldehyde equivalent is from 1:1 to 5:1, and more preferably from 1.2:1 to 1.3:1.

Ketone or aldehyde equivalent is understood to mean each keto or aldehyde group included in each molecule. Thus, a diketone will represent two equivalents, and will preferably be reacted with a minimum of two moles of peracetic acid.

As set forth above, the Baeyer-Villiger reaction scheme has been represented schematically as requiring the presence of water to convert an ester

to a hydroxy aromatic compound R'ArOH. As demonstrated in the Examples set forth below, the inventor has surprisingly found that the process of the present invention often produces some hydroxy aromatic compound R'ArOH, along with the corresponding ester

during the second stage of the reaction prior to the addition of water.

Although not shown in the Examples described below, at the end of the second reaction stage of the process of the present invention, sufficient water can be added to convert the ester

to the desired hydroxy aromatic compound R'ArOH. The water can be added during or, preferably, at the end of the second reaction stage.

During the addition of the aryl ketone and/or aromatic aldehyde to the peracetic acid solution, it is advantageous to add a homogeneous strong acid catalyst chosen from:
sulfuric acid
phosphoric acid
trifluoromethanesulfonic acid
methanesulfonic acid
trifluoroacetic acid or a heteroqeneous strong acid catalyst chosen from:
Amberlyst ® copolymer, marketed by Rohm & Haas
Nafion ® copolymer, marketed by Dupont.

Amberlyst ® copolymer, marketed by Rohm & Haas, is a copolymer of styrene with divinylbenzene that is crosslinked and of high molecular weight and which contains 4–6 milliequivalents of sulfonic function per gram of dry resin.

Nafion ® copolymer, marketed by Du Pont de Nemours, is a perfluorinated polymer of the formula:

$$[(CF_2-CF_2)_n-CF-CF_2]_x$$
$$(OCF_2CF)_mOCF_2CF_2SO_3H$$
$$CF_3$$

in which:
n is a number from 5 to 13.5,
m is an integer equal to 1, 2 or 3,
x has a value of approximately 1000.

The amount of acid catalyst added during the second stage is preferably such that the weight of the catalyst is from 5 to 20 percent of the weight of the peracetic acid.

The representative acid catalysts mentioned herein for addition during the second stage of the reaction are the same as those mentioned above for use in the first stage of the reaction. It is not necessary to add a strong acid catalyst during the second stage of the reaction. As shown in the Examples which follow, a strong acid catalyst is introduced in the first stage and no additional acid catalyst need be added during the second stage.

It is, however, preferable in cases where no strong acid catalyst is added during the second stage to add a quantity of aryl ketone and/or aromatic aldehyde during the second stage such that the weight of the strong acid catalyst from the first stage is from 5 to 20% of the weight of the peracetic acid.

The hydroxylated compounds produced by the present invention can be used in the pharmaceutical, plant-protection or polymer chemical industries.

The invention will be described more completely by means of the examples which follow, which must in no case be considered to limit the invention.

In the examples, the following abbreviations mean:

[O—O]: concentration of organic peroxides,
ww: weight/weight
DC: degree of conversion of the starting product $$\left(= \text{conversion} = \frac{\text{number moles converted}}{\text{initial number moles}} \times 100\right)$$

Yld: yield calculated on the converted product $$\left(= \text{selectivity} = \frac{\text{number moles of product} \times 100}{\text{number moles of reactant converted}}\right)$$

Φ: phenyl

EXAMPLE 1

1.58 g (16 mmol; 25.9 % ww) of 1,2-dichloroethane and 0.15 g (1.5 mmol; 2.5% ww) of concentrated sulfuric acid were introduced at 25° C. into a 30-cm³ teflon mini-reactor equipped with a bar magnet and a single-necked glass head with a side entry. After homogenization of the mixture, 0.64 g of a 70% strength aqueous hydrogen peroxide solution (H₂O₂: 0.45 g, 13 mmol, 7.4% ww; H2O 0.19 g, 11 mmol, 3.1% ww) was added using a syringe driver during 15 minutes and with efficient stirring. With temperature maintained at 25° C. using a water/ice bath, 2.45 g (24 mmol; 40.2% ww) of acetic anhydride was added over the course of 30 minutes, also with a syringe driver. The mixture was left with stirring for 45 minutes at 25° C. The distribution of the peroxide species was as follows (mol%): H₂O₂ 0%, AcO₂H 95%, AcOOAc 5%. The content of AcO₂H was 20% by weight.

The peracetic acid solution was heated to 40° C. and 1.28 g (10.3 mmol; 20.9% ww) of para-fluorobenzaldehyde was added using a syringe driver over the course of 45 minutes. A kinetic monitoring of the different species was carried out by high performance liquid chromatography. At the end of the inJection of the substrate, the following were obtained:

DC(p−FΦCHO)=92%

Yld(p−FΦOH)=Yld(p−FΦOCHO)+Yld(p−-FΦOH)=91%
YLD(p−FΦCO₂H)=9%.

If the same temperature and stirring conditions were maintained for a further 75 minutes (overall reaction time =2 hours), the following would be obtained:

$DC(p=F\Phi CHO)=97\%$ $Yld(p-F\Phi OH)=89\%$ $Yld(p-F\Phi CO_2H)=9\%.$

EXAMPLE 2

(comparative Example No. 1)

The procedure was as in Example 1, but with the order of addition substrate/oxidizing agent being reversed. Thus, the peracetic acid solution, when prepared, was introduced into a 10 cm³ glass syringe equipped with a double wall (maintained at approximately 0° C. by a continuous circulation through a water/ice bath), and added gradually to the para-fluorobenzaldehyde placed beforehand in the teflon mini-reactor and heated to 40° C. After a reaction time of 4 hours, the following were obtained:

$DC(p-F\Phi CHO)=81\%,$ $Yld(p-F\Phi OH)=69\%,$ $Yld(p-F\Phi COH)=26\%.$

EXAMPLES 3 to 7

The procedure was as in Example 1 but with different homogeneous acid catalysts (see attached table 1).

EXAMPLES 8 to 16

The procedure was as in Example 1, but with heterogeneous acid catalysts (see attached table 2).

EXAMPLE 17

The procedure was as in Example 1, but with para-fluorobenzaldehyde replaced by para-fluoroacetophenone and sulfuric acid replaced by trifluoromethanesulfonic acid (triflic acid). The temperature was 40° C. and the reaction time 4 hours.

$DC(p-F\Phi COMe)=85\%$ $Yld(p-F\Phi OH)=92\%$ $Yld(p-F\Phi CO_2H)=b\ 3\%$

EXAMPLES 18 to 22

The procedure was as in Example 17, but with different homogeneous acid catalysts (see attached table 3).

EXAMPLES 23 to 30

The procedure was as in Example 17 but with heterogeneous acid catalysts (see attached table 4).

EXAMPLE 31

Oxidation of para-phenylbenzaldehyde to caraphenylphenol (4-monohydroxybiphenyl)

The procedure was as in Example 1. The temperature was 40° C. and the substrate was added over the course of 20 minutes in the form of a solution at a concentration of 33.4% ww in 1,2-dichloroethane. The reaction time was 30 minutes.

$DC(p-\Phi\Phi CHO)=85\%$ $Yld(p-\Phi\Phi OH)=91\%$ $Yld(p-\Phi\Phi CO_2H)=3\%.$

EXAMPLE 32

Oxidation of para-phenylacetophenone to parachenylphenol

The procedure was as in Example 1. The temperature was 40° C. and the substrate was added over the course of 25 minutes in the form of a solution at a concentration of 12.8% ww in 1,2-dichloroethane. The reaction time was 2 hours.

$DC(p-\Phi\Phi COMe)=88\%$ $Yld(p-\Phi\Phi OH)=89\%$ $Yld(p-\Phi\Phi CO_2H)=4\%.$

EXAMPLE 33

Oxidation of para-phenylbenzaldehyde to parachenylphenol

The procedure was as in Example 1. The temperature was 40° C. and the substrate was added over the course of 6 minutes. The reaction time was 8 minutes.

$DC(p-\Phi O\Phi CHO)=95\%$ $Yld(p-\Phi O\Phi CHO)=93\%$ $Yld(p-\Phi O\Phi CO_2H)=2\%.$

EXAMPLE 34

Oxidation of para-phenoxyacetophenone to caraphenoxyphenol

The procedure was as in Example 1. The temperature was 40° C. and the substrate was added over the course of 35 minutes in the form of a solution at a concentration of 49% ww in 1,2 dichloroethane. The reaction time was 1 hour.

$DC(p-\Phi O\Phi COMe)=92\%$ $Yld(p-\Phi O\Phi OH)=92\%$ $Yld(p-\Phi O\Phi CO_2H)=1\%.$

EXAMPLE 35

Oxidation of para,para'-diacetyldiphenyl ether to para, para'-dihydroxydiphenyl ether (double Baeyer-Villiger).

The procedure was as in Example 1. The mole ratios were, however, as follows: 0-0/substrate =4, meq H+/substrate =0.5.

The temperature was 40° C. and the substrate was added over the course of 20 minutes in the form of a solution at a concentration of 20.2% ww in 1,2-dichloroethane. The reaction time was 40 minutes.

$DC(p,p'-MeCO\Phi O\Phi COMe)=98\%$

Yld(p,p'—HOΦOΦOH)=89%

EXAMPLE 36

Oxidation of para-hydroxy-meta-methylacetophenone to methylhydroquinone

The procedure was as in Example 1. The temperature was 25° C. and the substrate was added over the course of 10 minutes in the form of a solution at a concentration of 11.7% ww in 1,2-dichloroethane. The reaction time was 2 hours.

DC(4-OH-3-Me-ΦCOMe) =86%

Yld(4-OH-3-Me-ΦOH) =98%

EXAMPLE 37

Oxidation of cara-acetoxy-meta-methylacetophenone to methylhydroquinone

The procedure was as in Example 1. The temperature was 40° C. and the substrate was added over the course of 10 minutes in the form of a solution at a concentration of 37.7% ww in 1,2-dichloroethane. The reaction time was 2.5 hours.

DC(4-AcO-3-Me-ΦCOMe) =82%,

Yld(4-OH-3-Me-ΦOH) =88%

(the selectivities with respect to hydroquinone diacetate and monoacetate were, respectively 47 and 41%).

EXAMPLE 38

Oxidation of para-methoxy-meta-methylacetophenone to methylhydroquinone monomethyl ether The procedure was as in Example 1. The temperature was 25° C. and the substrate was added over the course of 6 minutes. The reaction time was 2 hours.

DC(4-MeO-3-Me-ΦCOMe) =93%,

Yld(4-MeO-3-Me-ΦOH) =96%

(the selectivity with respect to the monomethyl ether monoacetate was 94%). EXAMPLE 39 Oxidation of para-methoxy-ortho-methyl-acetophenone to methylhydroquinone monomethyl ether The procedure was as in Example 1. The temperature was 25° C. and the substrate was added over the course of 5 minutes. The reaction time was 2 hours.

DC(4-MeO-2-Me-ΦCOMe) =93%,

Yld methylhydroquinone greater than 90% (selectivity with respect to the monomethyl ether monoacetate was 90%).

TABLE 1

Experiments 3 to 7

| Ex No | Acid catalyst | Mole ratios | | rt (hr) | DC (%) | | Yld (%) | | | Σyld[b] (%) |
|---|---|---|---|---|---|---|---|---|---|---|
| | | [0-0][a]/ Subst. | H + Cat./ Subst. | | [0-0] | Substrate | Ester + Phenol | "ArOH"[d] | ArCO$_2$H | |
| Ref. | None | 1.1 | 0 | 4 | 43 | 46 | 5 + 0 | 5 | 95 | 100 |
| 3 | H$_2$SO$_4$ | 1.2 | 0.13 | 0,8 | | 92 | 75 + 16 | 91 | 9 | 100 |
| | | | | 2,0 | 77 | 97 | 70 + 19 | 89 | 9 | 98 |
| | H$_2$SO$_4$[c] | 1.1 | 0.13 | 4 | 77 | 76 | 52 + 22 | 74 | 18 | 92 |
| 4 | MeSO$_3$H | 1.1 | 0.11 | 4 | 82 | 87 | 64 + 7 | 71 | 30 | 100 |
| 5 | F$_3$CSO$_3$H | 1.2 | 0.15 | 2 | 68 | 67 | 44 + 31 | 75 | 7 | 82 |
| 6 | F$_3$CCO$_2$H | 1.1 | 0.12 | 4 | 65 | 73 | 10 + 0 | 10 | 90 | 100 |
| 7 | H$_3$PO$_4$ | 1.3 | 0.15 | 4 | 65 | 84 | 11 + 2 | 13 | 86 | 99 |

[a][0-0] = mole CH$_3$COO$_2$H + mole CH$_3$COO$_2$COCH$_3$;
[b]Σyld = overall result on substrate;
[c]Only AcOH as solvent, no ClCH$_2$CH$_2$Cl;
[d]"ArOH" is the sum of ester and phenol. Transformation of the ester into phenol can be routinely accomplished by one of ordinary skill in the art, such as by adding water.

TABLE 2

Experiments 8 to 16

| Ex No | Acid catalyst | Mole ratios | | rt (hr) | DC (%) | | Yld (8) | | | Σyld (%) |
|---|---|---|---|---|---|---|---|---|---|---|
| | | [0-0][a]/ Subst. | H + Cat./ Subst. | | [0-0] | Substrate | Ester + Phenol | "ArOH" | ARCO$_2$H | |
| Ref. | None[b] | 1.1 | 0 | 4 | 43 | 46 | 5 + 0 | 5 | 95 | 100 |
| 3 | H$_2$SO$_4$[g] | 1.2 | 0.13 | 2 | 77 | 97 | 70 + 19 | 89 | 9 | 98 |
| 8 | Amberlyst 15-H | 1.1 | 0.25 | 4 | 95 | 79 | 56 + 21 | 84 | 14 | 98 |
| 9 | Amberlyst 15-H | 1.1 | 0.06 | 1,8 | 79 | 71 | 76 + 4 | 80 | 16 | 96 |
| 10 | Amberlyst 15-H | 1.0 | 0.11 | 4 | 97 | 84 | 72 + 14 | 86 | 14 | 100 |
| 11 | Amberlyst 15-H | 1.1 | 0.13[c] | 1,8 | 87 | 74 | 70 + 9 | 79 | 20 | 99 |
| 12 | [d]Amberlyst 15-H | 1.1 | 0.13 | 4 | 96 | 82 | 1 + 74 | 75 | 15 | 90 |
| 13 | [e]Amberlyst 15-H | 1.2 | 0.13 | 2 | 87 | 99 | 75 + 11 | 87 | 13 | 100 |
| 14 | [f]Amberlyst 15-H | 1.3 | 0.15 | 2 | 95 | 91 | 77 + 10 | 87 | 11 | 98 |
| 15 | Nafion 117-H | 1.0 | 0.12 | 4 | 86 | 58 | 29 + 43 | 72 | 11 | 83 |
| 16 | Nafion 117-H | 1.3 | 0.06 | 2 | 83 | 99 | 76 + 15 | 91 | 8 | 99 |

[a][0-0] = mole CH$_3$COO$_2$H + mole CH$_3$COO$_2$COCH$_3$;
[b]reference experiment;
[c]recycled catalyst of Example 10;
[d]solvent = CH$_2$Cl$_2$, is removed after adding the substrate;
[e]time taken to add the substrate = 10 minutes;
[f]time taken to add the substrate = 45 minutes;
[g]Example of invention from Table 1.

TABLE 3

Experiments 18 to 22

| Ex No | Acid catalyst | Mole Ratios [0-0]$^{(a)}$/ Subst. | H + Cat./ Subst. | rt (hr) | DC (%) [0-0] | DC (%) Substrate | Yld (%) Ester + Phenol | "ArOH" | ArCO$_2$H | Σyld (%) |
|---|---|---|---|---|---|---|---|---|---|---|
| 18 | None | 1.1 | 0 | 4.5 | 3 | 4 | 41 + 0 | 41 | 60 | 100 |
| 19 | H$_2$SO$_4$$^{(b)}$ | 1.1 | 0.1 | 4 | 86 | 68 | 35 + 29 | 64 | 15 | 79 |
| 20 | MeSO$_3$H | 1.0 | 0.14 | 4 | 57 | 33 | 55 + 17 | 71 | 19 | 90 |
| 17 | F$_3$CSO$_3$H | 1.5 | 0.15 | 4 | 71 | 85 | 66 + 26 | 92 | 3 | 95 |
| 21 | F$_3$CCO$_2$H | 1.1 | 0.12 | 4 | 10 | 7 | 75 + 0 | 75 | — | 75 |
| 22 | H$_3$PO$_4$ | 1.2 | 0.17 | 4 | 5 | 8 | 87 + ε | 87 | 12 | 99 |

$^{(a)}$[0-0] = mole AcO$_2$H + mole AcO$_2$Ac;
$^{(b)}$Only AcOH as solvent.

TABLE 4

Experiments 23 to 30

| Ex No | Acid catalyst | Mole Ratios [0-0]$^{(a)}$/ Subst. | H + Cat./ Subst. | rt (hr) | DC (%) [0-0] | DC (%) Substrate | Yld (%) Ester + Phenol | "ArOH" | ArCO$_2$H | Σyld (%) |
|---|---|---|---|---|---|---|---|---|---|---|
| Ref | None$^{(a)}$ | 1.1 | 0 | 4.5 | 3 | 4 | 41 + 10 | 41 | 60 | 100 |
| 19 | H$_2$SO$_4$$^{(b)}$ | 1.1 | 0.1 | 4 | 86 | 68 | 35 + 29 | 64 | 15 | 79 |
| 23 | Amberlyst 15-H | 1.0 | 0.12 | 4 | 60 | 43 | 85 + 8 | 93 | 4 | 97 |
| 24 | Amberlyst 15-H | 1.1 | 0.24 | 4 | 78 | 25,6 | 56 + 13 | 69 | 9 | 78 |
| 17 | F$_3$CSO$_3$H$^{(a)}$ | 1.5 | 0.15 | 4 | 71 | 85 | 66 + 26 | 92 | 3 | 95 |
| 25 | Nafion 117H | 1.1 | 0.06 | 4 | 68 | 70 | 82 + 14 | 96 | 3 | 99 |
| 26 | Nafion 117H | 1.1 | 0.13 | 4 | 84 | 76 | 63 + 20 | 83 | 2 | 85 |
| 27 | Nafion 117H | 2.1 | 0.04$^{(c)}$ | 5 | 42 | 76 | 77 + 18 | 96 | 3 | 99 |
| 28 | Nafion 117H | 1.5 | 0.06$^{(c)}$ | 4 | 63 | 85 | 80 + 17 | 97 | 2 | 99 |
| 29 | Nafion 117H | 1.1 | 0.13$^{(c)}$ | 4 | 78 | 74 | 74 + 23 | 97 | 2 | 99 |
| 30 | Nafion 117H | 2.1 | 0.14$^{(c)}$ | 5 | 64 | 99 | 67 + 28 | 95 | 3 | 98 |

$^{(a)}$reference experiment;
$^{(b)}$Example of invention taken from Table 3 using only AcOH as solvent;
$^{(c)}$recycled catalyst of Example 26.

I claim:

1. A process for preparing a hydroxylated aromatic compound by the Baeyer-Villiger reaction, comprising:
   in a first stage, preparing a solution of peracetic acid by adding acetic anhydride to a solution of hydrogen peroxide in the presence of a strong acid catalyst; and
   in a second stage, adding an aryl ketone or an aromatic aldehyde or both to the solution of peracetic acid and maintaining the medium at a temperature below or equal to 40° C., for a time sufficient to obtain said hydroxylated aromatic compound, wherein each of the aryl ketone and the aromatic aldehyde is a compound of formula (I):

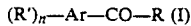
   (R')$_n$—Ar—CO—R (I)

in which
   Ar is a mono- or polycyclic, homo- or heterocyclic aromatic radical,
   R40 is selected from the group consisting of alkyl radicals containing from 1 to 4 carbon atoms, alkoxy radicals containing from 1 to 4 carbon atoms and hydroxy, halo, acyloxy, alkoxycarbonyl, perhaloalkyl, perhaloalkoxy, nitro, phenyl and phenoxy radicals, wherein said phenyl and phenoxy radicals are unsubstituted or substituted with a substituent selected from the group consisting of hydroxyl, formyl, acyloxy, and halo,
   n is an integer equal to 0, 1 or 2, and
   R is selected from the group consisting of hydrogen, an alkyl group containing 1 to 4 carbon atoms and a phenyl group.

2. The process as claimed in claim 1, wherein said first reaction stage additionally includes an aliphatic solvent having 1 to 6 carbon atoms and at least one halogen substituent.

3. The process as claimed in claim 2, wherein the aliphatic solvent is dichloroethane.

4. The process as claimed in claim 2, wherein a maximal amount of hydrogen peroxide is used in aqueous solution at a concentration of 70%, corresponding to the formation of a solution containing at most 35% by weight of peracetic acid and no longer containing free hydrogen peroxide.

5. The process as claimed in claim 4, wherein the maximal amount of hydrogen peroxide used corresponds to the formation of a solution containing from 15 to 25% by weight of peracetic acid.

6. The process as claimed in claim 5, wherein said solution contains approximately 20% by weight of peracetic acid.

7. The process as claimed in claim 1, wherein the radical Ar is a benzene ring.

8. The process as claimed in claim 1, wherein the compound of formula (I) is fluoroacetophenone.

9. The process as claimed in claim 1, wherein the compound of formula (I) is para-fluorobenzaldehyde.

10. The process as claimed in claim 1, wherein R' is a halo atom, Ar is benzene and R is hydrogen or methyl.

11. The process as claimed in claim 10, wherein R' is a fluorine atom.

12. The process as claimed in claim 2, wherein, in the second stage, the aryl ketone and/or aromatic aldehyde is added in an amount such that the ratio of the number of moles of peracetic acid per ketone or aldehyde equivalent ranges from 1:1 to 5:1.

13. The process as claimed in claim 12, wherein the molar ratio of peracetic acid to ketone or aldehyde equivalent is from 1.2:1 to 1.3:1.

14. The process as claimed in claim 2, wherein, during the second stage, a strong acid catalyst selected from sulfuric acid, trifluoromethanesulfonic acid, trifluoroacetic acid, phosphoric acid, methanesulfonic acid, Amberlyst ® copolymer and Nafion ® copolymer is added.

15. A process as claimed in claim 14, wherein the strong acid catalyst is selected from sulfuric acid, trifluoromethanesulfonic acid and Nafion ® copolymer.

16. The process as claimed in claim 15, wherein the weight of the strong acid catalyst added during the second stage is from 5 to 20 percent of the weight of the peracetic acid.

17. The process as claimed in claim 2, wherein said strong acid catalyst is selected from sulfuric acid, trifluoroacetic acid, methanesulfonic acid, trifluoromethanesulfonic acid, phosphoric acid, Nafion ®copolymer and Amberlyst ® copolymer.

18. The process as claimed in claim 1, wherein water is added during or at the end of said second reaction stage.

19. The process as claimed in claim 1, wherein the amount of acetic anhydride is in excess relative to the hydrogen peroxide such that neither water nor the hydrogen peroxide remains in the final solution.

* * * * *

UNITED STATES PATENT AND TRADEMARK OFFICE
CERTIFICATE OF CORRECTION

PATENT NO. : 4,950,809

DATED : August 21, 1990

INVENTOR(S) : Michel Gubelmann

It is certified that error appears in the above-identified patent and that said Letters Patent is hereby corrected as shown below:

Claim 1, column 11, line 55, "R40" should be --R'--.

Signed and Sealed this

Second Day of February, 1993

Attest:

STEPHEN G. KUNIN

*Attesting Officer*　　*Acting Commissioner of Patents and Trademarks*